US007282463B2

(12) United States Patent
Chang

(10) Patent No.: US 7,282,463 B2

(45) Date of Patent: Oct. 16, 2007

(54) THERMOCAUTERY BLOCK

(76) Inventor: Chieh Ming Chang, 7-3 Floor, No. 122, Omei Street, Wah-Hua Dist., Taipei (TW)

( * ) Notice: Subject to any disclaimer, the term of this patent is extended or adjusted under 35 U.S.C. 154(b) by 346 days.

(21) Appl. No.: 10/990,858

(22) Filed: Nov. 18, 2004

(65) Prior Publication Data

US 2006/0106439 A1 May 18, 2006

(51) Int. Cl.

*C04B 35/48* (2006.01)
*A61F 7/00* (2006.01)
*A61F 7/12* (2006.01)

(52) U.S. Cl. ........................ 501/107; 607/96; 607/108; 607/109; 607/110; 607/111; 607/114; 165/10

(58) Field of Classification Search ................ 501/107; 607/108–111, 114, 96; 165/10

See application file for complete search history.

(56) References Cited

U.S. PATENT DOCUMENTS

| | | | | |
|---|---|---|---|---|
| 4,743,726 | A * | 5/1988 | Hughes et al. | 219/759 |
| 5,086,629 | A * | 2/1992 | Dibrell | 62/259.3 |
| 5,494,598 | A * | 2/1996 | Hughes | 252/70 |
| 6,972,029 | B2 * | 12/2005 | Mayrhofer et al. | 607/114 |
| 2004/0243203 | A1 * | 12/2004 | Lavine | 607/114 |

* cited by examiner

*Primary Examiner*—Karl Group

(57) ABSTRACT

A thermocautery block is formed by mixing alumina, zirconium silicate, feldspar, pottery stone, siliceous limestone, kaolin, Gairome clay (Japan), and black soil with water; evenly stirring the mixture; compressing, dehydrating, and extruding the mixture into polygonal blocks; and drying, kilning, and cooling the blocks. The thermocautery block has a high density and a hardness higher than 6.0, and could store thermal energy after being heated for a short time. The stored thermal energy is progressively released via superficial areas of the block other than corners thereof to produce the effect of progressive temperature rise.

2 Claims, 3 Drawing Sheets

3

2

1

THERMOCAUTERY BLOCK

FIELD OF THE INVENTION

The present invention relates to a thermocautery block, and more particularly a thermocautery block that provides an effect of progressive temperature rise and is convenient for use.

BACKGROUND OF THE INVENTION

In traditional Chinese medicine, there are several ways for reducing flatulency and hematoma that cause discomfort at different body areas. These ways are generally divided into warm moxibustion, thermocautery stick, acupuncture with moxibustion, and heated suction cup, and are normally therapeutically effective in rehabilitation.

In warm moxibustion, sliced ginger is positioned over a patient's skin at an uncomfortable area, and moxa is positioned on the sliced ginger and ignited to produce heat, which advantageously reduces hematoma or waste gas inside the patient's body to achieve therapeutic effect in rehabilitation. The warm moxibustion must be handled and controlled by a doctor of Chinese medicine or a professional person to avoid burning of skin by the ignited moxa.

Thermocautery stick is frequently used in Chinese medicine to reduce hematoma. In doing so, the thermocautery stick is ignited and located over a patient's skin at an uncomfortable area with a proper distance left between the stick and the patient's skin. The ignited thermocautery stick must not contact with the patient's skin during the therapy. Again, the thermocautery stick must be handled and controlled by a doctor of Chinese medicine or a professional person to avoid burning of skin by the ignited thermocautery stick that is too closely positioned over the patient's skin.

In acupuncture with moxibustion, a needle is directly inserted into a patient's skin at an acupuncture point, so that energy is concentrated at the needle tip corresponding to the acupuncture point to thereby reduce the hematoma or waste gas. The acupuncture with moxibustion must absolutely be handled by a certified doctor of Chinese medicine. And, time control is also an important factor in acupuncture with moxibustion to achieve good therapeutic effect.

Suction cups used in Chinese medicine may be bamboo or wood suction cups, which are heated by roasting and then directly covered on a patient's skin at specific areas to diffuse or reduce hematoma thereof. Since the heated suction cup involves complicate operating procedures, it must be handled by a professional person, too.

All the above-described traditional therapies for rehabilitation in Chinese medicine employ heat transfer to expel waste gas and reduce hematoma from the patient's body. And, to obtain good therapeutic effect and avoid burning of skin or other undesired sequelae, it is a must these therapies be handled by a doctor or a professional person, particularly when the area to be treated is not easily accessible by the patient, such as the patient's back.

It is therefore tried by the inventor to develop a large-area and repeatedly usable thermocautery block that is able to store thermal energy after being roasted for a short time, and progressively release the stored thermal energy to produce progressive temperature rise and long-lasting thermocautery action, so that a user may conveniently handle the thermocautery block by himself in rehabilitation without the help of a professional person or a doctor.

SUMMARY OF THE INVENTION

A primary object of the present invention is to provide a repeatedly usable thermocautery block that is able to store thermal energy after being roasted for a short time, and progressively release the stored thermal energy to produce progressive temperature rise and long-lasting thermocautery action in rehabilitation.

Another object of the present invention is to provide a thermocautery block that could be conveniently handled by a user himself for use at different places on the user's body to achieve improved therapeutic effect in rehabilitation.

To achieve the above and other objects, the thermocautery block of the present invention is produced by blending alumina, zirconium silicate, feldspar, pottery stone, siliceous limestone, kaolin, Gairome clay (Japan), and black soil to form a high-density polygonal block having a hardness of more than 6.0, so that thermal energy could be stored in the block after the latter is heated for a short time and then progressively released from superficial areas of the block other than corners thereof.

The thermocautery block of the present invention is enclosed in a suitable bag, which is provided at least at an end with a string for holding by the user to facilitate convenient moving of the block over the user's skin.

The thermocautery block of the present invention is formed through the following steps: mixing alumina, zirconium silicate, feldspar, pottery stone, siliceous limestone, kaolin, Gairome clay (Japan), and black soil with water; evenly stirring the mixture; squeezing and dehydrating the mixture to form a lump; extruding the lump into shaped pieces; stirring and compressing the shaped pieces into polygonal blocks; drying the polygonal blocks; kilning the blocks by slow combustion up to 1200~1300° C.; and cooling the blocks to obtain a finished product of the thermocautery block each.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein FIG. 1 schematically shows a thermocautery block according to an embodiment of the present invention.

DETAILED DESCRIPTION OF THE PREFERRED EMBODIMENTS

Figure 1:
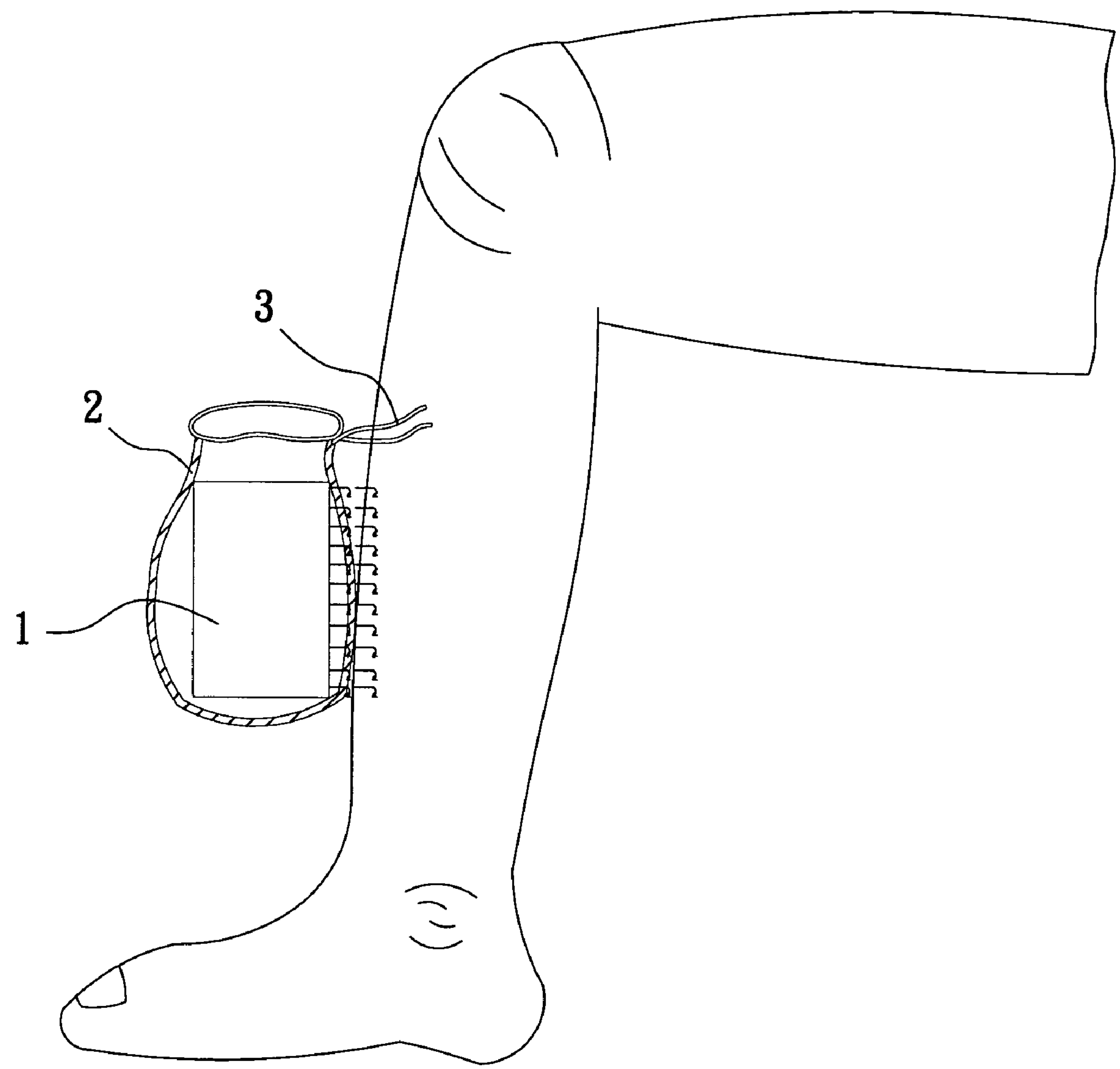

Please refer to FIG. 1 that is a schematic view showing a thermocautery block 1 according to an embodiment of the present invention and an application thereof. The thermocautery block 1 is a high-density polygonal block formed from a plurality of blended materials, including alumina 15~50 wt %, zirconium silicate 5 wt %, feldspar 26 wt %, pottery stone 8 wt %, siliceous limestone 4 wt %, kaolin 20 wt %, Gairome clay (Japan) 7 wt %, and black soil 5 wt %. In the illustrated embodiment, the thermocautery block 1 is in the form of a rectangular block. The thermocautery block 1 of the present invention has a hardness higher than 6.0, and could have thermal energy stored therein after it is heated for a short time. The stored thermal energy is progressively released from superficial areas of the block other than corners thereof, so as to provide an effect of progressive temperature rise. The thermocautery block 1 may be enclosed in a bag 2, which is provided at an open end with a string 3 or the like for holding by a user.

The purpose of forming the thermocautery block 1 into a rectangular block is to provide multiple corners on the block and accordingly, an effect of insulation at the corners. The corners on the thermocautery block 1 divide the superficial areas of the block 1 into several separated heat diffusing areas, so that the stored thermal energy is released from the block 1 at a reduced speed. Moreover, the high density and high hardness of the thermocautery block 1 also allow the block 1 to have a slowed heat dissipation speed to facilitate the progressive release of stored thermal energy from the block 1.

Figure 2:
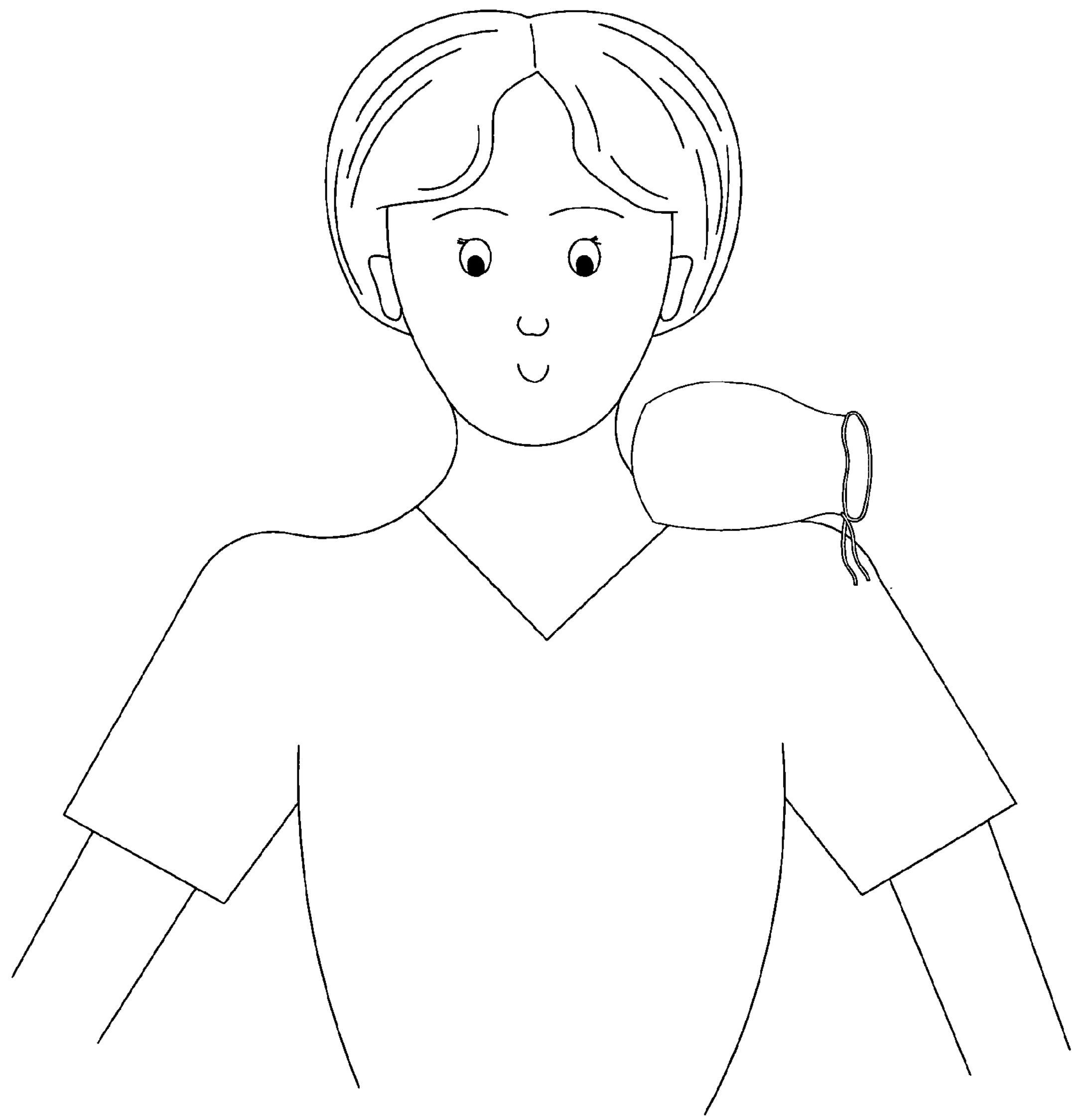
FIG. 2 schematically shows an example of application of the thermocautery block of the present invention.

When the thermocautery block 1 of the present invention is heated by roasting for about seven minutes at a half hour before using of it, it is able to release thermal energy for about one and a half hours. A user may put the roasted thermocautery block 1 in the bag 2 and then position it at a desired location on the skin, as shown in FIGS. 1 and 2. Since the thermocautery block 1 of the present invention provides large contact areas, it is more convenient for use in reducing hematoma or waste gas from the user's body. Moreover, the user may freely move the thermocautery block 1 over different areas on the skin in rehabilitation to avoid undesired burning of skin due to progressively increased temperature of the block 1. When the stored thermal energy is completely released, the block 1 could be roasted again for a short time and then used repeatedly. That is, the thermocautery block 1 of the present invention provides long-lasting effect and could be repeatedly used.

Figure 3:
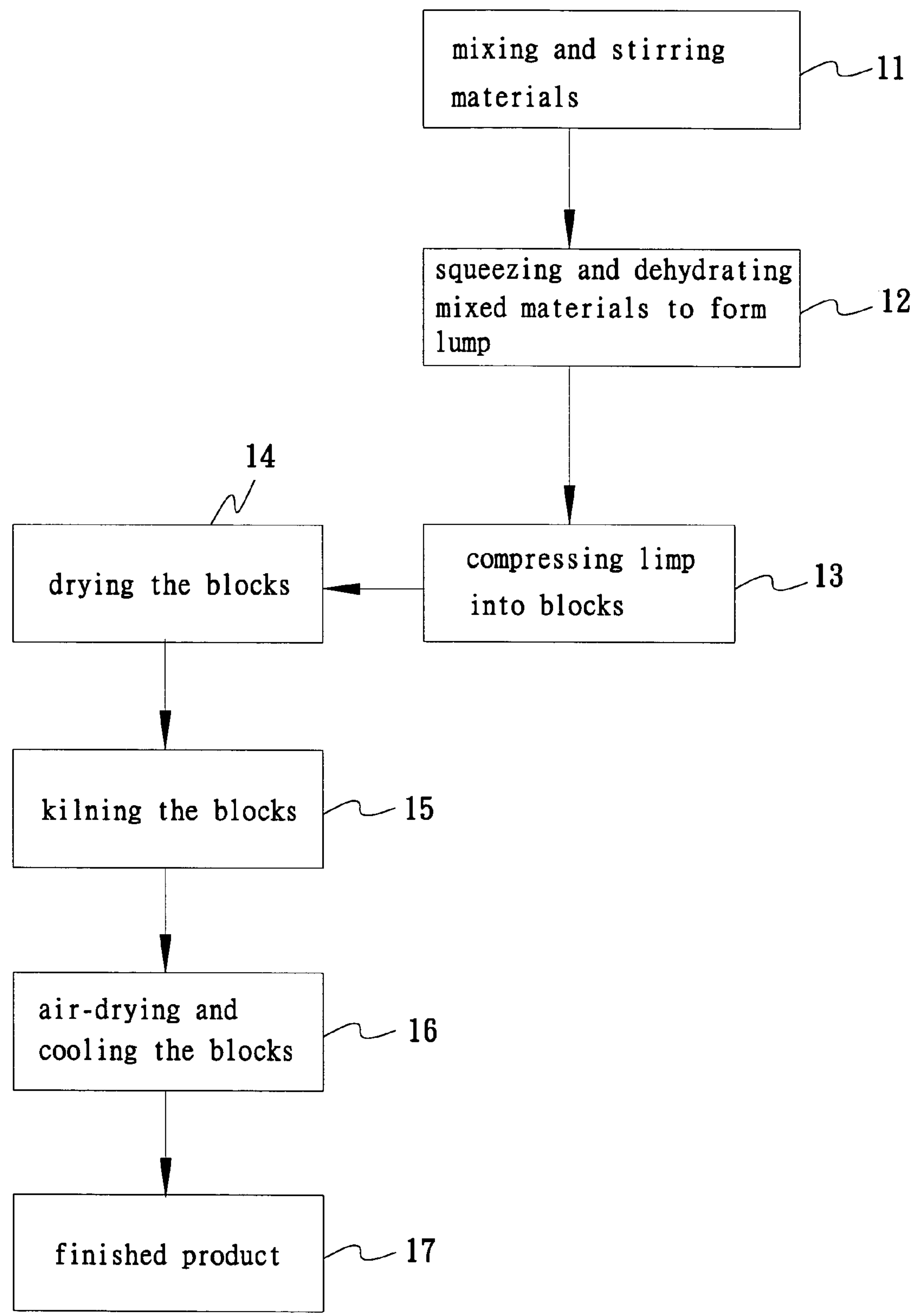
FIG. 3 is a flowchart showing the steps of producing the thermocautery block of the present invention.

FIG. 3 is a flowchart showing the steps of producing the thermocautery block 1 of the present invention. In Step 11, different materials, including alumina 15~50 wt %, zirconium silicate 5 wt %, feldspar 26 wt %, pottery stone 8 wt %, siliceous limestone 4 wt %, kaolin 20 wt %, Gairome clay (Japan) 7 wt %, and black soil 5 wt %, are mixed with water and evenly stirred for about four hours until all the materials are completely blended.

In Step 12, the blended materials are compressed into lump and dehydrated by squeezing water from the lump.

In Step 13, the compressed and dehydrated materials are stirred again and then vacuum extruded into bars, which are then compressed into polygonal blocks, such as rectangular blocks.

In Step 14, the polygonal blocks are positioned in an airy environment and air-dried for about two days.

In Step 15, the air-dried polygonal blocks are subjected to kilning through slow combustion at a temperature up to 1200~1300° C.

In Step 16, the kilned blocks are positioned at room temperature for cooling naturally.

In Step 17, the cooled blocks provide finished products of the thermocautery blocks of the present invention.

In summary, the thermocautery block 1 of the present invention has the following advantages: (a) it needs only a short time of roasting to provide a long-lasting effect in use; (b) it provides a moderate thermocautery effect through progressive temperature rise; (c) it could be operated and freely moved in the process of rehabilitation without the need of being handled by a professional person or a doctor; (d) it allows repeated and convenient use thereof; and (e) it is able to store and progressively release the stored thermal energy to enable improved therapeutic effect in rehabilitation.

What is claimed is:

1. A thermocautery block, comprising a rectangular bock formed by mixed different materials, including alumina 15-50 wt %, zirconium silicate 5 wt %, feldspar 26 wt %, pottery stone 8 wt %, siliceous limestone 4 wt %, kaolin 20 wt %, gairome clay (Japan) 7 wt %, and black soil 5 wt %, with water and evenly stirring the mixture;

compressing and dehydrating the mixture into lump;

stirring the compressed and dehydrated lump again and then vacuum extruding the lump into bars, which are then compressed into polygonal blocks;

putting the polygonal blocks in the an airy environment for air drying;

kilning the air-dried polygonal blocks through slow combustion at a temperature up to 1200-1300° C.; and allowing the kilned blocks to cool at room temperature naturally to provide a finished block that has a high density and a hardness of more than 6.0, and is able to store thermal energy after being heated for a short time and progressively release the stored thermal energy via superficial areas of the finished block other than corners thereof to create a progressive temperature rise.

2. The thermocautery block as claimed in claim 1, wherein said finished block is enclosed in a bag, which is provided with at least a holder, such as a string, at one end of the bag for holding purpose.

* * * * *